United States Patent [19]

Okamoto et al.

[11] Patent Number: 4,833,930
[45] Date of Patent: May 30, 1989

[54] METHOD OF SAMPLING STEEL MATERIAL AND A DEVICE THEREFOR

[75] Inventors: Kaizo Okamoto; Akira Ichihara; Akimune Sato; Kenji Hirata; Katsuhisa Hirayama; Eiji Hina; Shigeru Nakaji; Minoru Sakamoto; Takashi Tanaka; Keizo Shimizu, all of Kurashiki, Japan

[73] Assignees: Kawasaki Steel Corp., Hyogo; Nippon Air Brake Co., Ltd., Kobe, both of Japan

[21] Appl. No.: 79,142

[22] Filed: Jul. 28, 1987

[30] Foreign Application Priority Data

Feb. 10, 1987 [JP] Japan .................. 62-29370

[51] Int. Cl.⁴ .............................. G01N 1/08
[52] U.S. Cl. .................. 73/864.45; 73/864.42; 83/919; 356/36
[58] Field of Search ........... 73/864.41, 864.42, 864.44, 73/864.45; 83/919; 356/313, 66

[56] References Cited

U.S. PATENT DOCUMENTS

| | | | |
|---|---|---|---|
| 715,631 | 12/1902 | Ayres | 73/864.44 |
| 1,397,541 | 11/1921 | Owens | 73/864.44 X |
| 1,996,534 | 4/1935 | Baker | 73/864.41 X |
| 3,779,646 | 12/1973 | Hancart et al. | 356/36 X |
| 3,791,743 | 2/1974 | Cody et al. | 356/36 X |
| 3,876,306 | 4/1975 | Onodera et al. | 356/313 |
| 4,058,017 | 11/1977 | Tsujimoto et al. | 73/864.31 |
| 4,281,546 | 8/1981 | Fraleigh | 73/864.44 |
| 4,518,051 | 5/1985 | Sollie et al. | 73/864.45 |
| 4,594,885 | 6/1986 | Rodger | 73/864.45 X |
| 4,653,336 | 3/1987 | Vollweiler | 73/864.44 |

FOREIGN PATENT DOCUMENTS

| | | | |
|---|---|---|---|
| 372471 | 3/1973 | U.S.S.R. | 73/864.45 |
| 521494 | 7/1976 | U.S.S.R. | 73/864.44 |
| 1177713 | 9/1985 | U.S.S.R. | 73/864.41 |

*Primary Examiner*—Tom Noland
*Attorney, Agent, or Firm*—Bierman and Muserlian

[57] ABSTRACT

A method and a device for collecting a quantoback analysis sample in hot state from a preferred position of a continuously cast steel piece are disclosed. According to this invention, a dish like recess is cut on the surface of cast steel piece while leaving a center column, then the root of left center column is root cut and taken out as sample. A cutting device and a way for accessing the cutting device are presented for operating this process.

2 Claims, 14 Drawing Sheets

METHOD OF SAMPLING STEEL MATERIAL AND A DEVICE THEREFOR

BACKGROUND OF THE INVENTION

This invention relates to a method of sampling steel material and its device, and more particularly to a method and a device for quickly sampling a composition analyzing specimen in hot state from a preferred position on the surface of a continuously cast piece held at a high temperature.

In the continuous casting technology, the qualities (composition) of cast steel piece in a non-stationary part, e.g., in a junction part between different kinds of steel materials being continuously cast, should be noted at a high temperature state of the cast piece in view of energy conservation and high productivity, particularly when the hot charge or direct sequential rolling operation is intended.

However, no established technology was available for online collecting test samples from a preferred position of a hot cast steel piece, in the prior art. Therefore, offline sampling was commonly used. Unfortunately, the offline sampling causes temperature drop of the cast steel piece, while traditional analyzing procedure using cut chips requires a long time for analyzing the components. Consequently, it was not possible to apply so-called hot charging to a furnace in which a red-hot, cast and cut steel piece, as conveyed from the casting machine, was directly transported into the heating furnace for saving additional heating energy required for succeeding hot rolling processing. In addition, it was also impossible to introduce the direct sequential rolling, as normally called, in which a red-hot, cast and cut steel piece was rolled directly or after being heated only at both ends whose temperature might drop more quickly.

Regarding the method of rapid component analyzing, there is known a quantoback system in which a small block specimen is prepared from steel material for spectro analyses. According to the quantoback system, the quantometer (photoelectric directly reading type spectro-analyzer) is used for spectroanalysis. With this system, analyzed results can be indicated on a meter, after solving the inconvenience associated with conventional spectro-analyzers. Various types of the quantoback systems are available, such as production control models or research purpose models.

SUMMARY OF THE INVENTION

An object of the present invention is to provide a new technology with which samples for the quantoback, in a diameter of 10 mm to 25 mm and a height of 10 mm to 25 mm in lump form, can be online collected from a preferred position of a cast steel piece maintained at a high temperature of 900° to 1200° C.

Another object of the present invention is to establish a method of quickly sampling test specimens, for example within 150 seconds per position.

Still another object of the present invention is to offer a method described above, where created cut chips, in danger of high temperature and clogging the rotating shaft, etc. as continuously created during cutting work, can be discarded in safety.

Another object of this invention is to present an excellent practicing device in which, when the test sample is collected by laterally cutting the root of the sample at the end period of root-cutting operation, the laterally cut portion will not be ruptured by cutting force.

Furthermore, it is another object of the present invention to provide a shape of the recess, remaining on the cast steel piece after completion of collecting a sample, will not adversely affect the product qualities after rolling work.

Still another object of the present invention is to present a device that can easily achieve all methods above.

In order to accomplish the foregoing objects, the following technical means are introduced in the present invention.

(1) A lump-form sample is collected from the surface of steel material by high-speed cutting.

(2) A first process, where a recess like a dish-shaped groove ring leaving a cylindrical non-cut part at the center thereof is formed by cutting on a surface portion of steel material, is sequentially followed by a second process in which said cylindrical non-cut part, left at the center is cut at its root portion for separation.

(3) Cut chips created during cutting operation with steel material, especially with a high-temperature cast piece, have large ductility which lowers workability because cut chips are created in a continuous tape form. Therefore, so-called step feed operation is carried out for higher efficiency to discard cut chips, in which the cutting bit is fed while operating reciprocal motion in feeding direction, for separating cut chips in shorter sections.

(4) Said recess, left on the surface of the steel material after completion of sampling, is shaped in a gentle sloped shallow dish having a diameter larger than 6 times its depth.

The foregoing technical means of this invention provide the following functions. A sample for quantoback analysis can be collected from a preferred position on the surface of an online steel material maintained at high temperature by high-speed cutting. The said means of the present invention also realize the hot charge and the direct sequential rolling for continuously cast steel material. Other items, to be improved according to the scope of this invention, include significant improvement of quality control accuracies and higher degrees of energy saving and productivity.

DETAILED DESCRIPTION OF THE PREFERRED EUBODIMENTS

Figures 3A, 3B:
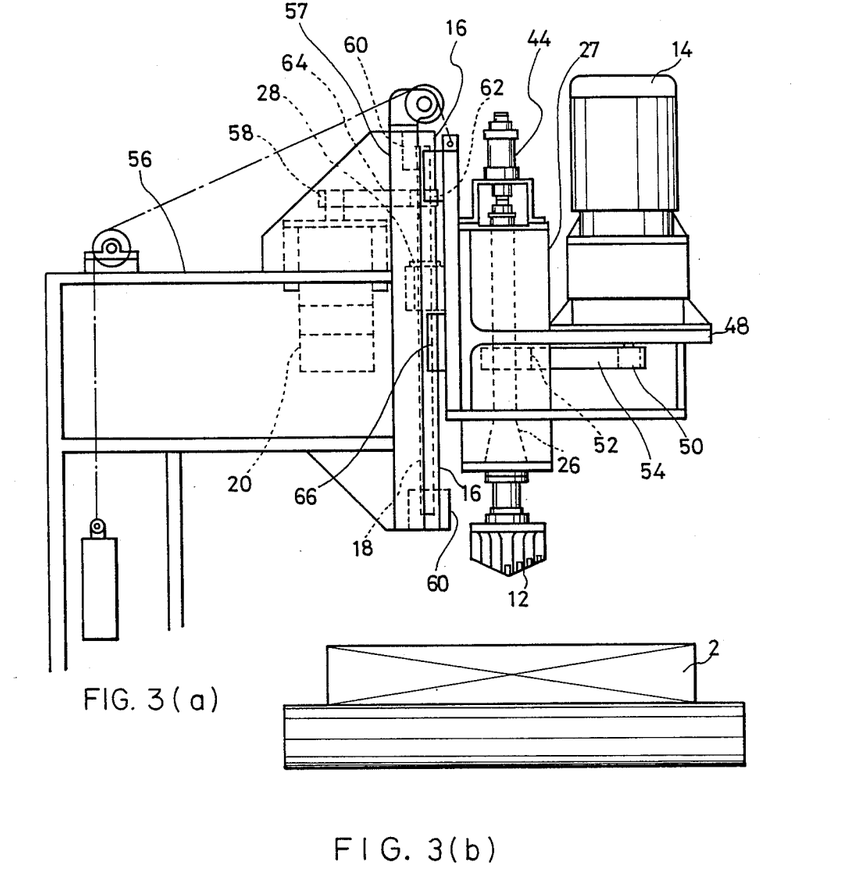
FIGS. 3(a) and 3(b), (hereafter collectively referred to as FIG. 3), 4, and 5 show a sampling device which can advantageously execute a method of this invention, with FIGS. 3 through 5 illustrating side, front and plan views, respectively.
Figure 4:
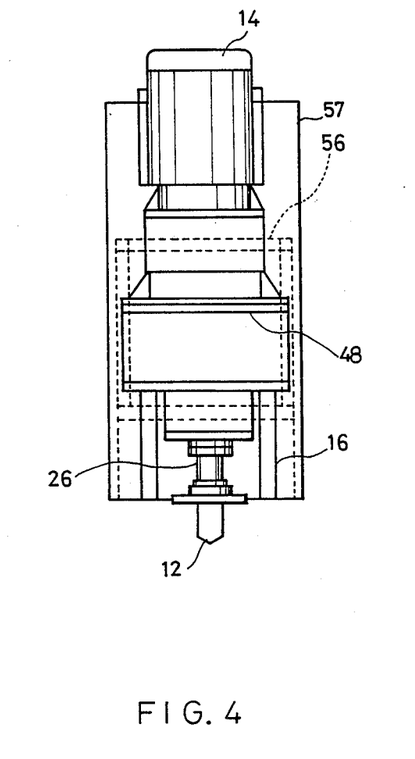
Figure 5:
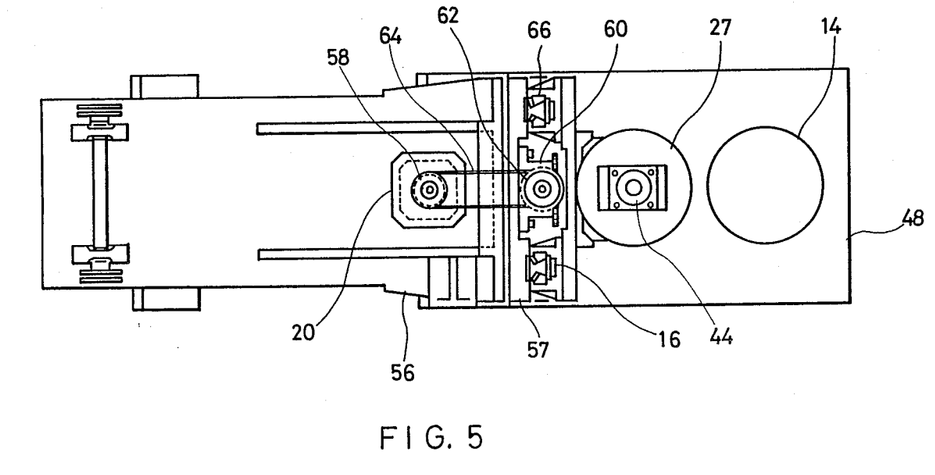

FIGS. 3 through 5 show entire views of a device advantageously used for executing a method of the present invention. FIGS. 6 through 10 denote its partial details. An embodiment of this invention, using this device, will be described in detail as follows.

This device comprises a cutting tool 12 for cutting a cast steel piece, a motor 14 for driving the main shaft of cutting tool 12, a motor 20 for feeding cutting tool 12 in a manner of such as stepping feed, a tool post feed shaft 18 for the tool post driving system and a feed mechanism 28.

Main unit 27, comprising main shaft 26 of cutting tool (super-hard alloy tip) 12, is fixed in up/down rack 48 on which motor 14 for driving the main shaft is equipped. A belt 54 (or a chain may substitute) is set in a spanned manner between pulley 50 of main shaft driving motor 14 and pulley 52 mounted on main shaft 26. Cutting tool 12 is rotatingly driven by motor 14 according to the present invention. A hydraulic cylinder 44 is located on the upper end of main shaft 26.

On the other hand, a tool post feed shaft 18, with male screws, is rotatably borne by bearings 60 which are fixed in the upper and lower parts of support frame 56. In the upper part of said shaft 18, a pulley 62 is fixed. In addition, a cutting tool feed motor 20, available for forward and reverse rotations, is mounted on said support frame 57. A timing belt 64 (or a chain may substitute) is spanned between pulley 58 of motor 20 and pulley 62 for said tool post feed shaft 18. Thus, tool post feed shaft 18 is forwardly or reversely rotated by rotating forwardly or reversely tool feed motor 20, through pulley 58, belt 64 and pulley 62.

Tool post feed shaft 18, provided with male threads, is engaged with a feed mechanism 28 with female threads.

Feed mechanism 28 is integrated with up/down rack 48. Therefore, when tool post feed shaft 18 is forwardly or reversely rotated by motor 20, said up/down rack that supports main shaft driving motor 14 and cutting tool 12 is driven up or downward. Thereby, cutting tool 12 can be fed up or down.

A guide rail 16 is provided in the vertical direction on both sides of support frame 57, for guiding a slide bearing 66 fixed on up/down rack 48. Thus, up/down rack 48 can smoothly move up and down.

FIGS. 6 through 10 show the detail of cutting tool 12. Referring to FIGS. 6–10, a shank 30 is mounted in a taper hole (not illustrated) in main unit 27. In the lower part of body 31, connected to shank 30, a pair of cutting tool mounting bases 70 are arranged in a row in both sides of the center of flange 68. On the top of tip mounting base 70, a cutting tip (super-hard alloy tip) 32, for cutting a recess around the sample, is fixed with bolt 72.

Figure 6:
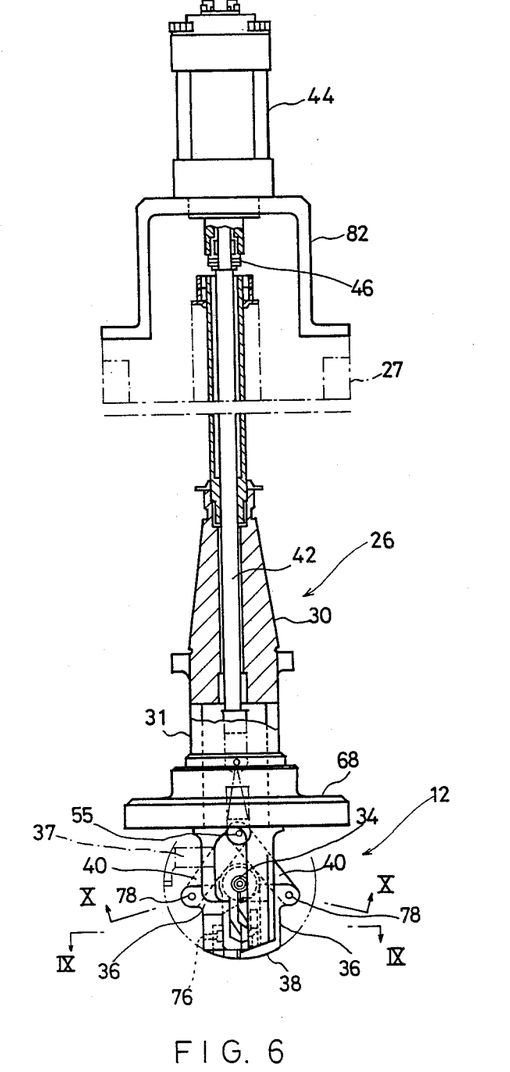
FIG. 6 shows the side view of a cutting tool while FIG. 7 illustrating its front view.
Figure 7:
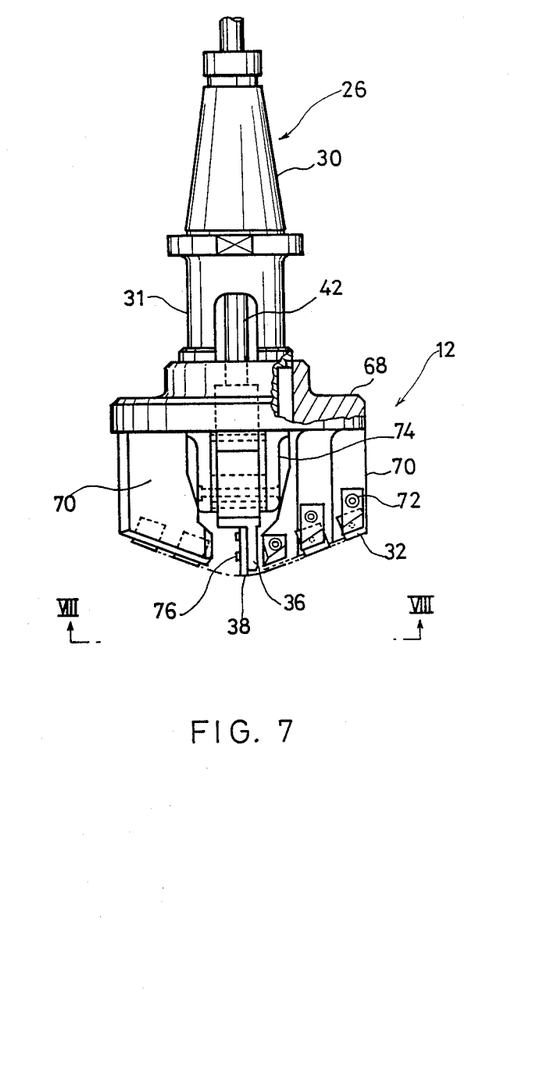
Figure 8:
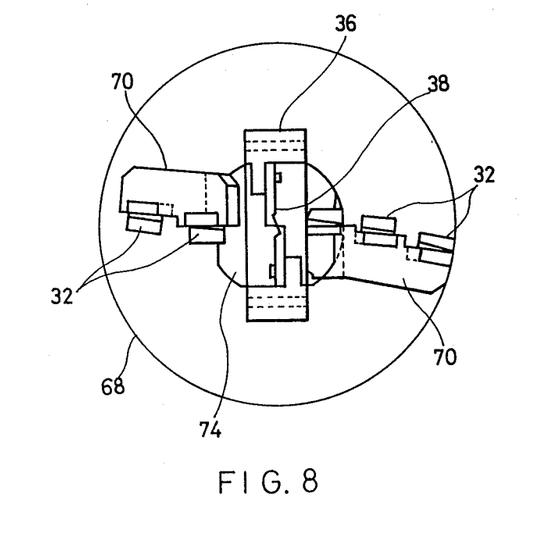
FIGS. 8, 9 and 10 show the VIII—VIII view of FIG. 7, IX—IX and X—X views of FIG. 6 respectively.
Figure 9:
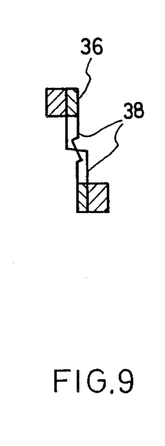
Figure 10:
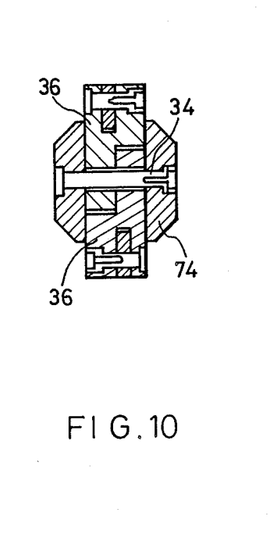

According to the shown illustrations, three tips 32 are mounted on one tip mounting base 70 while two tips 32 being equipped on the other base 70. These tips are arranged with suitable intervals in radial direction to prevent discontinuation of cut recesses on the steel material.

A pair of bearings 74 is mounted in the lower part of flange 68 in such a position substantially orthogonal to said pair of tip mounting bases 70 (see FIGS. 8 and 10), while a pair of arms 36 being supported on bearings 74 through pins 34 in a freely rotable manner. In addition, a root cutting tip (super-hard alloy tip) 38 is mounted at the top of each arm 36 by means of bolt 76. At the side end of each arm 36, one end of a pair of links 40 is connected by pin 78. The other end of link 40 is connected to the top part of rod 42 by means of pin 55.

A hydrolic cylinder 44 is supported on the upper portion of main shaft 26 by means of support frame 82. This hydraulic cylinder 44 is connected to rod 42.

Figure 1A:
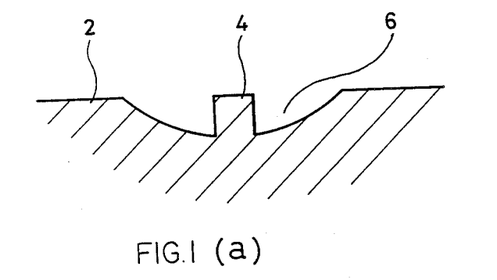
FIGS. 1(a) and 1(b) shows the processes of an embodiment of the present invention.
Figure 2:
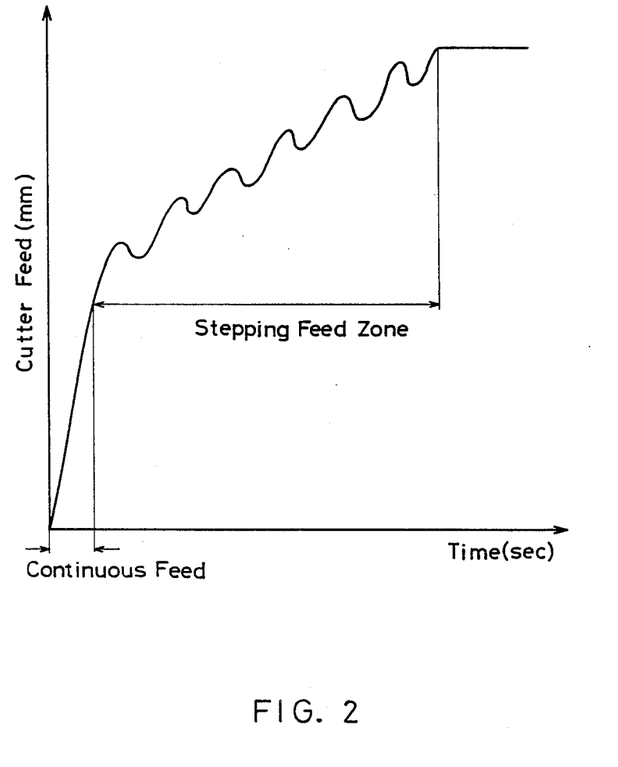
FIG. 2 shows a graph for the stepping feed in the first process of the present invention.

Cutting tip 32 is used to cut dish type ring form recess groove 6 of FIG. 1(a). Cutting tip 32 rotates around center axis of the cutting shaft while cutting. Referring to FIG. 2, the cutting tip is fed up to the surface of cast steel piece at high speed and further fed reciprocally stepping while cutting, thereby easily cutting dish type ring recess groove 6 with a cylindrical sample 4 for analysis left at the center of the groove.

A cutting tip 38 for sample 4 remained in the above in cylindrical form is provided with arm 36 that can open and close to from position 37 around pin 34. The cutting tool consists of a root cutting tip 38 fixed on arm 36, a link 40 for rotating arm 36, a rod 42 for moving link 40 up and down and a hydrolic cylinder 44 for moving up and down rod 42. A composit needle bearing 46 is equipped on the piston rod of hydrolic cylinder 4, for bearing thrust.

The present invention is embodied using the foregoing components. First, recess groove 6 is cut around the cast steel piece 2 as shown in FIG. 1(a). At this time hydraulic cylinder 44 pulls up rod 42 while arm 36 escaping in a position 37 (see FIG. 6). In this state, main shaft 26 is rotated by motor 14 while feeding in steps to cut recess groove 6 around sample 4 shown in FIG. 1(a) in specified depth.

Figure 1B:
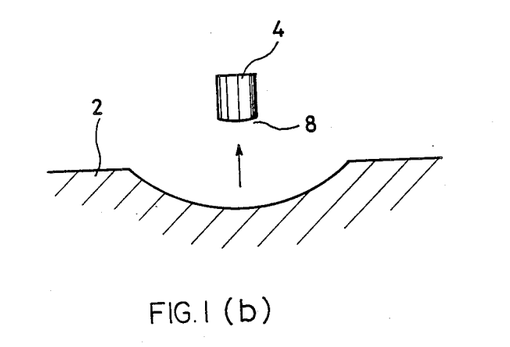

Next, feeding is stopped and, while main shaft 26 being rotated, hydraulic cylinder 44 is operated to gradually push down rod 42 to located arm 37 to position 36 (FIG. 6) while piercing sample cutting tip 38 into the root (root cutting part 8 show in FIG. 1(b)) of sample 4 for root cutting the sample After completion of cutting sample root cutting part 8, the rotation of main shaft 26 is stopped while driving feed mechanism 28, tool post feed shaft 18 and tool feed motor 20 with tip 38 still holding the sample, thereby driving up main shaft 26. Then the sample collecting device is moved to a specified position where rod 42 is pulled up by means of hydraulic cylinder 44 while opening arm 36 to release holding of sample 4 that is thus collected. (See FIG. 1(b))

Now another embodiment of the present invention is described in detail as follows.

Figure 11A:
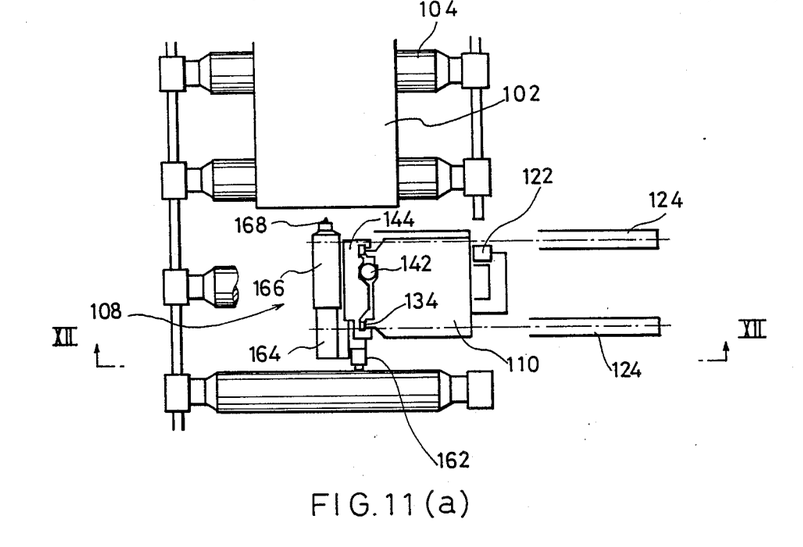
FIG. 11(a) is the plan view of another embodiment of the sampling device based on the present invention.
Figure 11B:
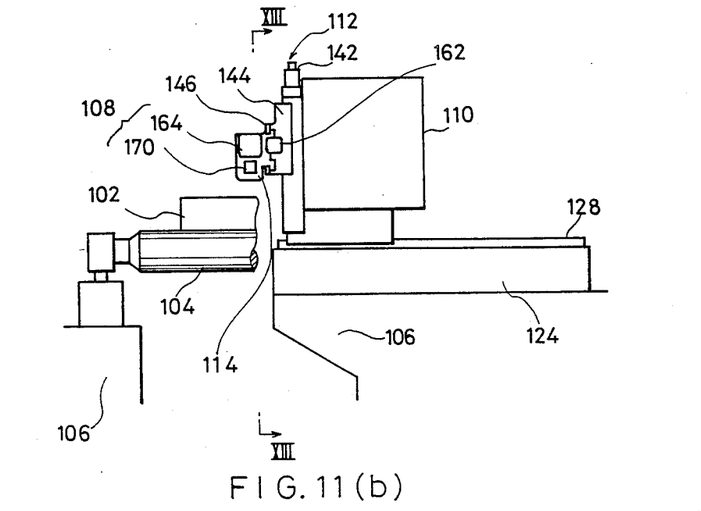
FIG. 11(b) shows its side view while FIG. 12 denoting XIII—XIII view of FIG. 11(b).

The preferred second embodiment comprises a tool device 108, a main body 110 that moves in horizontal direction orthogonally to the running direction of roller table 104, an up/down device 112 that drives tool device 108 in the up/down direction and a horizontal drive device 114 that moves horizontally in the running direction of roller table 104.

Figures 15, 16:
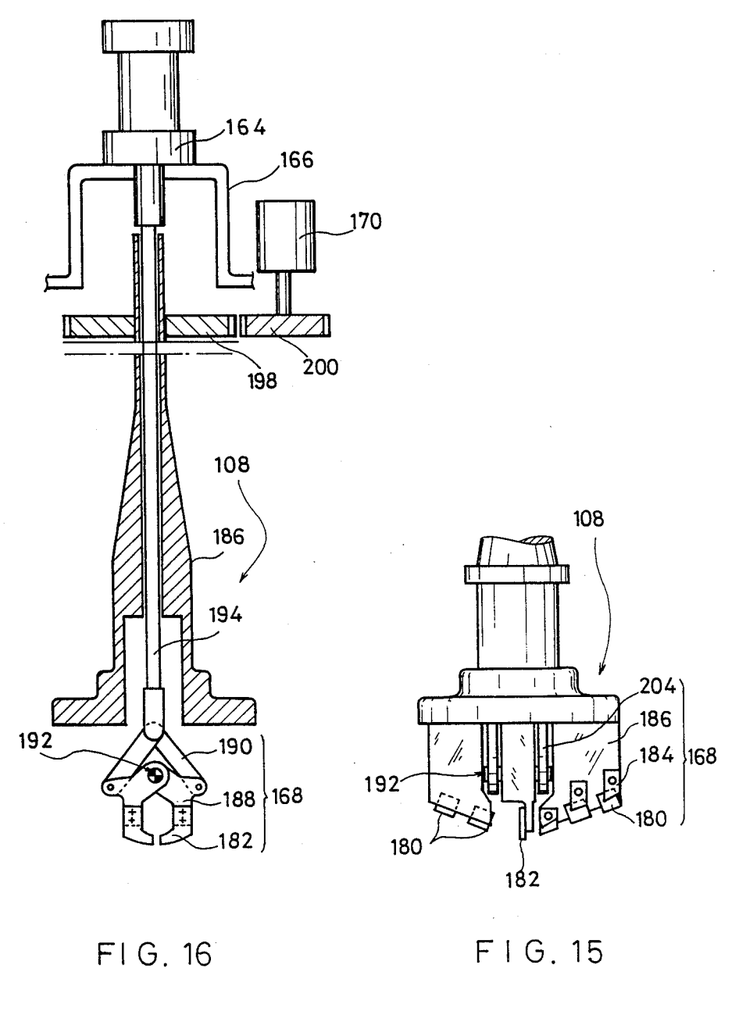
FIG. 15 is a vertical plan of the spot facing tool.
FIG. 16 shows a vertical plan of the root cutting tool.

Referring to FIGS. 15 and 16, tool device 108 comprises a tool post 166, a tool 168, a tool rotating device 170, a sample cutting drive device 164, tips 180, 182, a tip holder 186, etc. The functions of tool device 108 is described together with cutting process. Sampling comprises processes of face cutting and root cutting.

First the face cutting process is described. Tip 180 of face cutting tool is fixed on tip holder 186 by means of tip holder 184. Tip holder 186 is connected to rotating device 170 through gears 198, 200. Therefore, tip holder 186 is rotated by starting up rotating device 170. Then, a dish recess is face cut leaving a center portion, on the cut end part of cast piece 102 by driving horizontal drive device 162 of FIG. 11.

Next, when specified cutting namely face cutting is completed, root cutting drive device 164 is activated with tip holder 186 held still in face cutting completion state (position). With root cutting drive device 164 activated, root cutting tip 182 takes a state of FIG. 16 while performing root cutting at the root of the sample. Driving force of root cutting is transmitted from root cutting drive device 164 to tip 182 through connecting rod 194, link 190 and root cutting tip holder 188. Link 90 drives tip 182 to move with a rotating center of root cutting link pin 192 mounted on root cutting pin holder 204 supported by bit holder 186. As described above, rotating force for cutting is obtained from rotating device 170 while root cutting drive force being available from root cutting drive device 164.

Next, the device for driving the tool device is described in the following.

Main body 110, mounted rotatably in horizontal direction orthogonal to the direction of running for roller table 104, is placed on slide face 128 of rail rack 124 installed on foundation 106. The entire system is driven out of and inside of the installation line of roller table 104 by means of horizontal drive device 122.

Figure 13:
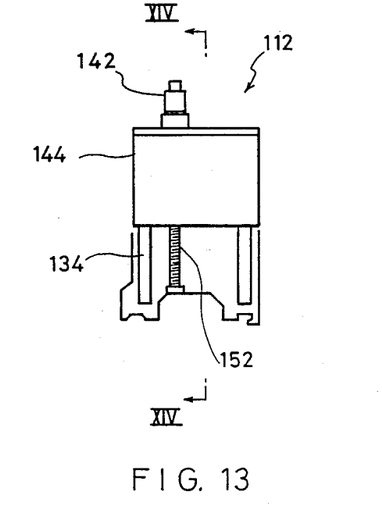
FIG. 13 is the side view of a device for moving up-/down its cutting tool.
Figure 14:
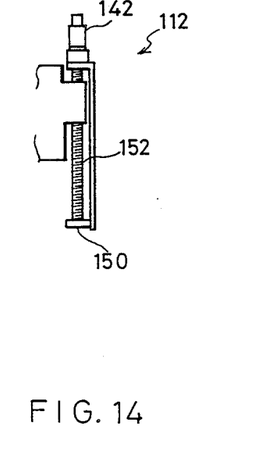
FIG. 14 is a view in arrow XIV—XIV of FIG. 13.

Up/down drive device 112, for moving up and down tool device 108, is shown in FIGS. 13 and 14 which illustrate XIII—XIII view of FIG. 11(b) and XIV—XIV view of FIG. 13, respectively. Up/down drive device 142 moves up and down moving block 144 on slide face 134 mounted on main unit 110 by rotating screw bar 152. Screw bar 152 is supported by bearings 150. Accordingly, tool device 108 is driven up and down.

Figure 12:
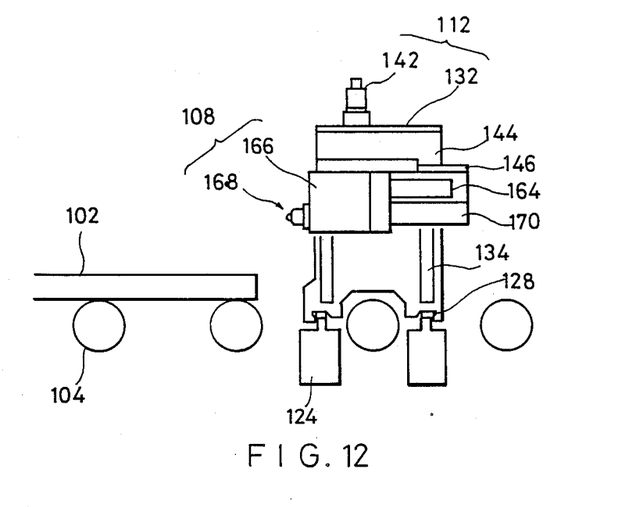

Referring to FIGS. 11 and 12, tool device 108 is driven horizontally in the same way by means of horizontal drive device 162 along slide face 146 mounted on moving block 144.

Under the configuration described above, sampling with the embodiment of the present invention is carried out as follows.

Cast steel place 102, as cast by a continuous casting machine, is cut to preferred lengths, conveyed to the position of this sampling device and then stopped. Accuracies for stopping, operated in the above, are normally similar to those (±30 mm) of ordinary roller table 104. Sampling device, waiting outside of the line of roller table, is moved into the scope of the table by means of horizontal drive device 122 and adjusted to positions t/4 and t/2 where t represents a thickness of cast steel piece, in the up/down direction of the tip under the control of up/down drive device 142, for preparing sampling operation to be done at the end face of cast piece 102. Next, the sampling device carries out cutting operation while moving bit tip onto the end face of the cast piece, by being driven with horizontal drive device 162. After completion of cutting, the sampling device is operated in the procedure reverse to the above and returns back in place for waiting. Collected sample is maintained in tip holder 186 and root cutting holder 188, and then discharged in the waiting position to another device while completing sampling operation.

Figure 17A:
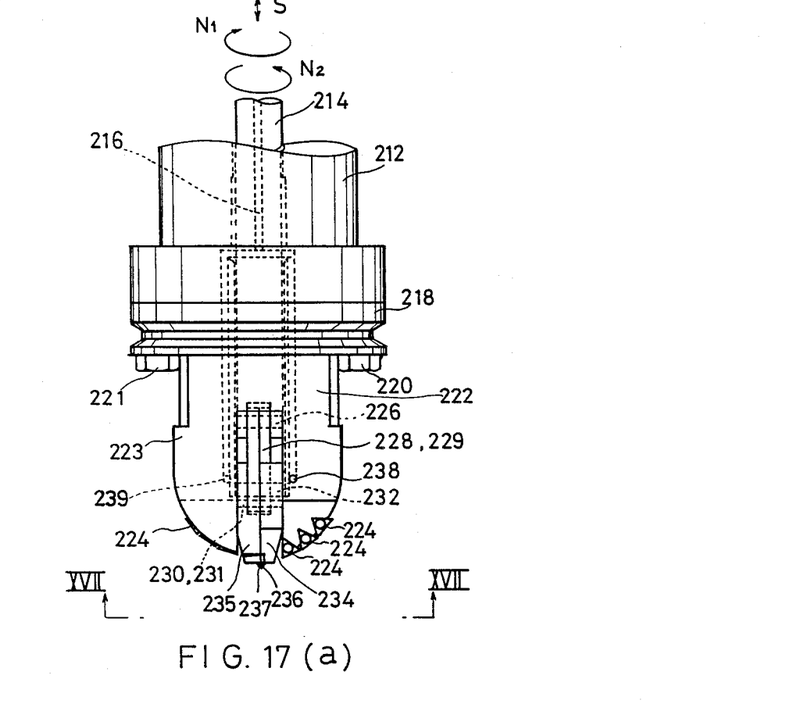
FIG. 17(a) indicates the general front view of a cutting tool based on a further preferred embodiment of the present invention.
Figure 17B:
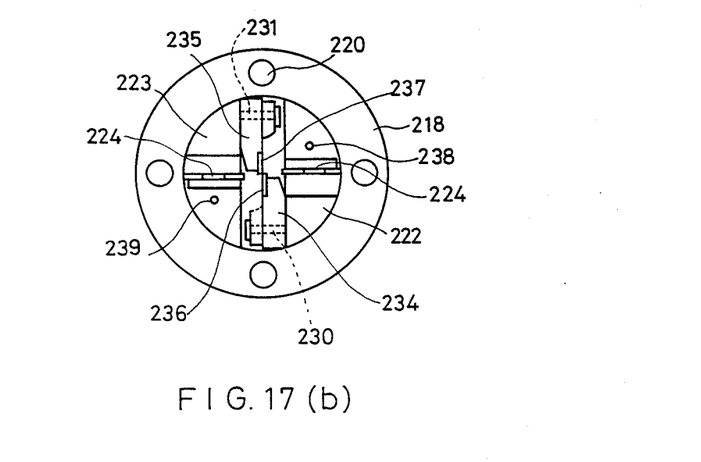
FIG. 17(b) shows the view in arrows XVII—XVII.
Figure 17C:
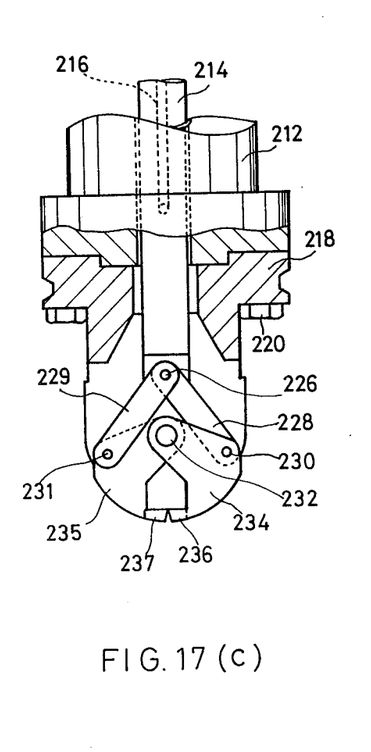
FIG. 17(c) illustrates a partial cutaway side view for showing open conditions of the root cutting tool.
Figure 17D:
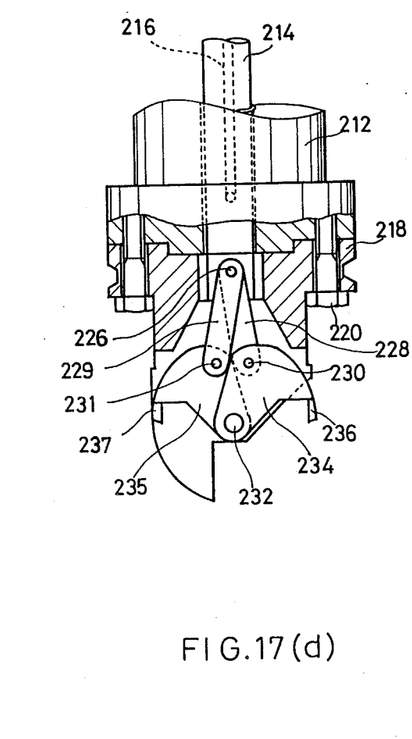

Another advantageous embodiment of the present invention is described in the following. Embodiment 3 is provided with a modified tool. FIG. 17(a) shows a front view of the cutting tool based on the present invention. FIG. 17(b) shows the XVII—XVII arrow view. FIG. 17(c) denotes a state with the root cutting tip held closed, in a side view. FIG. 17(d) relates to the side view for showing opened root cutting tip.

Main shaft 212, on which the bit is mounted, drives cutting tool unit 218 and face cutting tool mounting frame 222, 223 fixed onto said unit in the $N_1$ direction by a rotating power drive whose illustration is omitted herein. Rod 214, for driving rooting cutting tip frames 234, 235, can rotate simultaneously with the forward and reverse rotations in $N_1$ and $N_2$ of main shaft 212, while also being movable in up/down direction in stroke S.

Cutting tool unit 218 is mounted onto main shaft 212 by means of bolts 220, 221. Frames 222, 223 on which facing bits having tips of semi-spherical shape are fixed, are securely mounted on cutting tool unit 218. Pairs of said facing tips 224 are oppositely mounted on said facing tip frames 222, 223. In FIG. 17(a), three tips are mounted in one side, namely a total of 6 tips.

Referring to FIG. 17(c), rod 214 is connected to arms 228, 229 by means of pin 226, while connecting root cutting bit frames 234, 235 onto arms 228, 229 by means of pins 230, 231. Root cutting tip frames 234, 235 are fixed on facing tip frames 222, 223 by pin 232 with root cutting tips 236, 237 mounted on frames 234, 235 for root cutting. With the foregoing structure, root cutting tip frames 234, 235 freely move from root cutting state of FIG. 17(c) to the escape condition of FIG. 17(d) when rod 214 is moved in the direction of stroke S in relation to main shaft 212.

There is a passage 216 communicated to the top of bit unit 218 passing through rod 214, for supplying the bit with cutting oil and air. Holes 238, 239 are provided for supplying the cutting device with cutting oil and air.

Referring to FIG. 17(b), facing tip 224 in the side of cutting oil supply holes 238, 239 comprises a space deprived of quadrant parts, while facing tip frames 222, 223 being installed in the quadrant parts left in the side opposite to cutting oil supply holes 238, 239, said facing frames 222, 223 being prepared for mounting facing tip 224. Therefore, facing tip 224 is mounted in such a manner that cut chips, created during facing operation and discharged by facing tip 224, are led through the space deprived of quadrant parts.

In addition, root cutting tips 236, 237 are also mounted on root cutting tip frames 234, 235 in such a manner that cut chips are discharged in the direction to said space.

No detailed devices for mounting the cutting tool, driving the tool and processed cast steel piece, etc. are illustrated because no specified positional relations are required.

Now the procedure for operating the cutting tool device of the present invention is described as follows. For facing operation, refer to FIG. 17(d). Root cutting tips 236, 237 are pulled upwardly in escape position, then facing tip 224 is placed in contact with the upper face of cast steel piece, although not illustrated, thus main shaft 212 being rotated forwardly in $N_1$ direction.

The entire main shaft assembly is fed in this state onto the cast steel piece. Meanwhile, the steel piece is cut by facing tip 224 while discharging cut chips into the space without quadrant parts contained in the bit tip, namely into the side of cutting oil supply holes 238, 239 shown in FIG. 17(b), thus performing smooth cutting operation. When facing work proceeds completely with a degree of specified depth, main shaft 212 is once stopped together with returning main shaft 212 slightly. For next operation, refer to FIG. 17(c). While main shaft is rotated in the $N_2$ direction, reverse to $N_1$, rod 214 is pulled up in such a direction that root cutting tips 236, 237 are closed. Thus, root cutting tips 234, 235 are sequentially closed by means of pin 226, arms 228, 229, pins 230, 231, root cutting bit frames 234, 235 and pin 232, while cutting off the root of faced sample. At that time, cut chips, as discharged from root cutting tips 236, 237, are flowed into the side of cutting oil supply holes 238, 239 shown in FIG. 17(b), namely the space without quadrant parts. Thereby, smooth cutting is assured.

According to conventional systems known in the prior art, the end of root cutting operation was processed in such a manner that root cutting tips 236, 237 were totally kept in contact with the sample. In consequence, when the root of the sample, remaining uncut, becomes small, this uncut column is broken by the cutting force of the root cutting bit while leaving a small stud on the cut sample, like the pin of a spinning top. At the same time, cut chips also remain on this uncut column, together with long whiskers adhering on the cut sample. These whiskers used to disturb smooth collection of cut sample or smooth encasing of cut chips into trash box.

Figure 18:
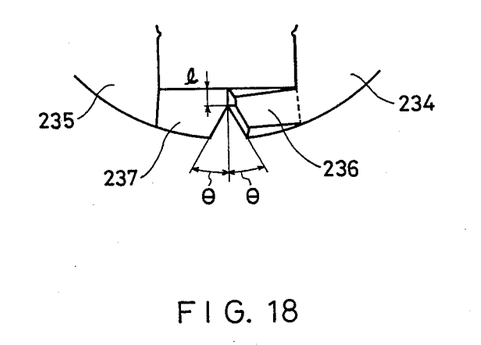
FIG. 18 is a partial side view for illustrating conditions of completed root cutting with the root cutting tool.

According to a principle of this invention for preventing such troubles as described above, a marginal part of about 1 to 2 mm length is left on each tip of root cutting tips 236, 237 as far as no troubles are caused for strength of said tips 236, 237. In addition, the relief of an angle of about 15° to 45° by 20 is provided at the top of each marginal part. Thus, said uncut column is no longer left at the end period of root cutting, while also completely free from adhesion of cut whiskers. The present invention brings about the following effects.

(a) Great energy saving effect is achieved because sampling operation can be performed in hot state with cast steel piece.

(b) Online sampling is enabled while forming the sample in a cylindrical shape which can be quantoback analyzed. Results can also be obtained more quickly than any other methods known in the prior art. Time to completion of the analysis becomes about 1/100 as long as the time required for conventional systems. In addition, sampling work can be completed within 150 seconds. Thus, no cast steel pieces remain unexamined in the process.

(c) Drilling work for sampling, required in conventional methods using warm pieces (at about 100° C.) is no longer required, resulting in higher safety of operator at work.

(d) Automatic sampling work is enabled yielding excellent labor saving.

(e) After completion of collecting sample, only a dish-like recess which may be vanished during subsequent rolling is left on the surface of cast steel piece. Therefore, the piece can be rolled flat in next process, while reducing the affect of the trace of sampling onto product qualities thereby increasing yield of the product.

(f) The present invention is advantageously applied to collecting samples for analyzing cast steel produced by the continuous casting system, used for the hot charge, etc. In addition, this invention is also applicable to sampling other types of steel materials. However, it should be noted that the stepping feed is not always required unless the ductility of cut chips is high for steel material in use.

(g) Sample, after collection, is free from cut chips or uncut column adhering or remaining. Accordingly, the sample collecting device based on the present invention can be operated automatically. Thereby, samples can be gathered automatically and online from hot cast steel pieces.

What is claimed is:

1. A method of sampling moving steel material comprising steps of:
   cutting down a dish-shaped groove ring around a column left at the center portion thereof on a surface of the moving steel material,
   cutting off the root of said column, and
   taking off the cut column for quantoback analysis thereof.

2. The method of sampling steel material of claim 1, in which a cutting tool is fed reciprocally stepping in the direction of a central feed axes thereof for cutting down said dish-shaped groove ring.

* * * * *